US009061985B2

(12) United States Patent
Matsuura et al.

(10) Patent No.: US 9,061,985 B2
(45) Date of Patent: Jun. 23, 2015

(54) METHOD FOR CONCENTRATING AQUEOUS 3-HYDROXY-2,2-DIMETHYLPROPANAL SOLUTION

(75) Inventors: Yutaka Matsuura, Okayama (JP);
Ikutaro Kuzuhara, Okayama (JP);
Masahiro Yamane, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 0 days.

(21) Appl. No.: 14/002,442

(22) PCT Filed: Mar. 2, 2012

(86) PCT No.: PCT/JP2012/055438
§ 371 (c)(1),
(2), (4) Date: Aug. 30, 2013

(87) PCT Pub. No.: WO2012/118196
PCT Pub. Date: Sep. 7, 2012

(65) Prior Publication Data
US 2013/0334028 A1 Dec. 19, 2013

(30) Foreign Application Priority Data
Mar. 3, 2011 (JP) .................................. 2011-046328

(51) Int. Cl.
*C07C 45/84* (2006.01)
*C07D 319/06* (2006.01)

(52) U.S. Cl.
CPC .............. *C07C 45/84* (2013.01); *C07D 319/06* (2013.01)

(58) Field of Classification Search
CPC ...... C07C 45/84; C07C 319/06; C07C 47/19; B01D 3/36
USPC .............. 203/17, 31, 63, 71, 73–85; 568/420, 568/700, 853, 854
See application file for complete search history.

(56) References Cited

U.S. PATENT DOCUMENTS

| | | | |
|---|---|---|---|
| 2,945,008 A | 7/1960 | Caldwell et al. | |
| 3,935,274 A | 1/1976 | Jacobsen et al. | |
| 4,134,879 A * | 1/1979 | Schmidt | 524/289 |
| 5,859,296 A * | 1/1999 | Neumann et al. | 562/580 |
| 6,201,159 B1 | 3/2001 | Choi et al. | |
| 2010/0113836 A1 | 5/2010 | Sirch et al. | |

FOREIGN PATENT DOCUMENTS

| | | |
|---|---|---|
| EP | 1568678 | 8/2005 |
| JP | 51-68514 | 6/1976 |
| JP | 1-299239 | 12/1989 |
| JP | 6-29206 | 2/1994 |
| JP | 7-215904 | 8/1995 |
| JP | 10-67704 | 3/1998 |
| JP | 2000-26356 | 1/2000 |
| JP | 2000-505103 | 4/2000 |
| JP | 2005-29563 | 2/2005 |
| JP | 2007-70339 | 3/2007 |
| JP | 2010-520250 | 6/2010 |
| WO | 98/17614 | 4/1998 |

OTHER PUBLICATIONS

"Ettore Santoro, Journal of the Chemical Society, Perkin Transactions II", , 1978, pp. 189-192, vol. 3.
International Search Report Issued May 1, 2012 in PCT/JP2012/055438.
Search report from E.P.O. in EP 12752976 6, mail date is Feb. 3, 2014.
"*3-Hydroxy-2,2-dimethylpropionaldehyde: Equilibria and Structure of its Dimer*", Santoro et al., Journal of the Chemical Society, Perkin Transactions II, Vo. 3, pp. 189-192, 1978.

* cited by examiner

*Primary Examiner* — Prem C Singh
*Assistant Examiner* — Brandi M Doyle
(74) *Attorney, Agent, or Firm* — Greenblum & Bernstein, P.L.C.

(57) ABSTRACT

The present invention provides a method for concentrating an aqueous solution containing at least 3-hydroxy-2,2-dimethyl propanal and/or a dimer thereof, which includes subjecting a mixed solution of an aqueous solution containing at least 3-hydroxy-2,2-dimethyl propanal and/or a dimer thereof and an azeotropic agent to azeotropic distillation in a distillation column to distil off water and the azeotropic agent from the mixed solution, wherein the mixed solution is prepared by adding, as the azeotropic agent, at least one selected from the group consisting of 1-butanol, 2-butanol, 2-methyl-1-propanol, 1-pentanol and 1-hexanol to the aqueous solution.

20 Claims, No Drawings

METHOD FOR CONCENTRATING AQUEOUS 3-HYDROXY-2,2-DIMETHYLPROPANAL SOLUTION

TECHNICAL FIELD

The present invention relates to a method for concentrating an aqueous solution of 3-hydroxy-2,2-dimethyl propanal (hereinafter referred to merely as "hydroxypivalaldehyde" or "HPA") and/or a dimer thereof in an efficient manner by distillation of the aqueous solution.

BACKGROUND ART

In general, HPA is synthesized by subjecting isobutylaldehyde and formaldehyde to an aldol condensation reaction in the presence of a basic catalyst.

The aldol condensation reaction may proceed either under acidic conditions or under basic conditions. However, since HPA contains a carbonyl group and a hydroxyl group in one molecule thereof, crystals of a dimer of HPA are condensed into a tetramer thereof under the acidic conditions. PTLs 1 and 2 disclose an aldol condensation reaction under basic conditions for the purpose of avoiding the condensation of the dimer of HPA into the tetramer.

After completion of the reaction, the resulting reaction product solution is subjected to distillation to remove low-boiling point components such as unreacted isobutylaldehyde and formaldehyde therefrom, thereby obtaining an aqueous solution containing HPA (hereinafter referred to merely as an "aqueous crude HPA solution"). HPA is frequently used as an intermediate product for synthesis of organic compounds such as neopentyl glycol and Spiro glycol, and as described in PTLs 3 and 4, the thus obtained reaction production solution may be used in subsequent steps without being subjected to any purification treatment.

Meanwhile, NPL 1 discloses that there is present an equilibrium relationship between a monomer of HPA and crystals of a dimer of HPA as shown in the following formula (1). Therefore, when HPA is subjected to crystallization purification, the HPA obtained as crystals are crystals of the dimer of HPA. The crystals of the dimer of HPA exhibit a reactivity substantially identical to that of the monomer of HPA as described in many literatures such as PTL 3, etc.

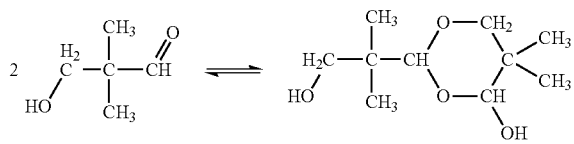

(1)

Also, there is disclosed a method in which the above aqueous crude HPA solution is diluted by adding water thereto, and then subjected to crystallization purification to obtain high-purity HPA (refer to PTLs 5 to 7). A filtrate obtained by subjecting a crystallization slurry to solid-liquid separation and by washing a filter cake contains uncrystalized HPA and/or a dimer of HPA. Such a filtrate may be reused as an intermediate product of organic compounds such as neopentyl glycol which can be produced without need of using high-purity HPA, or may be discarded.

The filtrate also contains a large amount of water. Therefore, in the case where the filtrate is reused as an intermediate product of the organic compounds, it may be sometimes required to previously remove water from the filtrate in view of deterioration in reaction efficiency, etc. Also, even when the filtrate is discarded, in view of a large load imposed on facilities for waste water treatments, it is preferred that the filtrate is separated into HPA and water before being discarded.

However, owing to such a fact that water and HPA have an azeotropic relation therebetween, there is a problem that it is difficult to remove only water from the filtrate by a distillation separation method to concentrate HPA in an efficient manner.

On the other hand, as the distillation separation technique, PTL 8 discloses a method of separating water from an aqueous hydroxypivalic acid solution by distillation using toluene or a mixture of toluene and 1-butanol, etc., as an azeotropic agent. PTL 9 discloses a method of producing Spiro glycol while subjecting HPA to azeotropic dehydration under reflux of toluene. However, PTLs 8 and 9 do not describe at all distillation separation between water and HPA and/or a dimer thereof. HPA has a chemical structure partially similar to those of hydroxypivalic acid and spiro glycol but contains different functional groups from those of hydroxypivalic acid and spiro glycol. Therefore, HPA has different properties from those of hydroxypivalic acid and spiro glycol. In general, in the case where water is separated from an aqueous solution by distillation using an azeotropic agent, the azeotropic agent capable of efficiently separating water from the aqueous solution may vary depending upon properties of substances dissolved in the aqueous solution. In consequence, the azeotropic agent to be used for the distillation separation must be carefully studied and selected in view of a system of the aqueous solution to be treated. Thus, an optimum azeotropic agent for a certain aqueous solution system is not necessarily an optimum azeotropic agent for another aqueous solution system, and therefore it is very difficult to predict an optimum azeotropic agent for a specific aqueous solution system.

PTL 10 discloses a method in which a mixed solution containing an aqueous sodium hydroxide solution, isobutylaldehyde, an aqueous formaldehyde solution and methanol is reacted to conduct an aldol condensation reaction between isobutylaldehyde and formaldehyde, and after completion of the aldol condensation reaction, methanol and unreacted isobutylaldehyde are removed from the obtained reaction product solution by azeotropic distillation. However, PTL 10 does not describe at all removal of water by the azeotropic distillation. In addition, in the aldol condensation reaction between isobutylaldehyde and formaldehyde as described in PTL 10, methanol that is unnecessary for the reaction is also added to the same reactor, so that a working efficiency of the reactor is considerably lowered, which results in industrially disadvantageous process.

CITATION LIST

Patent Literature

PTL 1: JP 7-215904A
PTL 2: JP 2000-26356A
PTL 3: JP 1-299239A
PTL 4: JP 2005-29563A
PTL 5: JP 6-29206B
PTL 6: JP 51-68514A
PTL 7: JP 2007-70339A
PTL 8: JP 10-67704A
PTL 9: U.S. Pat. No. 2,945,008B
PTL 10: U.S. Pat. No. 3,935,274B

Non Patent Literature

NPL 1: Ettore Santoro, Journal of the Chemical Society, Perkin Transactions II, Vol. 3, pp. 189-192, 1978

SUMMARY OF INVENTION

Technical Problem

An object of the present invention is to provide a method for concentrating an aqueous solution containing HPA and/or a dimer thereof in an efficient manner.

Solution to Problem

As a result of extensive and intensive researches on concentrating method of an aqueous solution containing HPA and/or a dimer thereof for solving the above conventional problems, the present invention has been accomplished.

That is, the present invention relates to a method for concentrating an aqueous solution containing HPA and/or a dimer thereof as defined in the following aspects (1) to (8).
(1) A method for concentrating an aqueous solution containing at least 3-hydroxy-2,2-dimethyl propanal and/or a dimer thereof, including subjecting a mixed solution of an aqueous solution containing at least 3-hydroxy-2,2-dimethyl propanal and/or a dimer thereof and an azeotropic agent to azeotropic distillation in a distillation column to distil off water and the azeotropic agent from the mixed solution, wherein the mixed solution is prepared by adding, as the azeotropic agent, at least one selected from the group consisting of 1-butanol, 2-butanol, 2-methyl-1-propanol, 1-pentanol and 1-hexanol to the aqueous solution.
(2) The method as described in the above aspect (1), wherein the azeotropic agent is at least one selected from the group consisting of 1-butanol and 2-methyl-1-propanol.
(3) The method as described in the above aspect (1) or (2), wherein the 3-hydroxy-2,2-dimethyl propanal and/or the dimer thereof are produced by an aldol condensation reaction between formaldehyde and isobutylaldehyde.
(4) The method as described in any one of the above aspects (1) to (3), wherein the aqueous solution containing at least 3-hydroxy-2,2-dimethyl propanal and/or a dimer thereof is an aqueous solution containing at lease one selected from the group consisting of the following (a) to (c):

(a) an aqueous 3-hydroxy-2,2-dimethyl propanal solution obtained by distilling off low-boiling point components including unreacted isobutylaldehyde from a reaction product solution produced by an aldol condensation reaction between an aqueous formaldehyde solution and isobutylaldehyde in the presence of a basic catalyst;

(b) a filtrate recovered by subjecting the aqueous solution (a) to crystallization, and the subjecting the resultant product to solid-liquid separation; and (c) an aqueous solution obtained by subjecting the aqueous solution (a) to crystallization, then subjecting the resultant product to solid-liquid separation, and then dissolving purified 3-hydroxy-2,2-dimethyl propanal recovered by the solid-liquid separation into water.
(5) The method as described in any one of the above aspects (1) to (4), wherein the azeotropic distillation is carried out at a column bottom temperature of from 82 to 120° C.
(6) The method as described in any one of the above aspects (1) to (5), further including obtaining a distillate from a top of the distillation column; and feeding, after the distillate is separated into two phases of an azeotropic agent phase and a water phase, a whole or part of the azeotropic agent phase back into the distillation column.
(7) The method as described in any one of the above aspects (1) to (6), wherein the distillation column is a multistage distillation column.
(8) The method as described in any one of the above aspects (1) to (7), further including adjusting a pH value of the aqueous solution containing at least the 3-hydroxy-2,2-dimethyl propanal and/or a dimer thereof to within a range of from 3.5 to 10.5.

Advantageous Effects of Invention

According to the present invention, when an azeotropic agent capable of undergoing azeotropy with water and incapable of undergoing azeotropy with HPA and/or a dimer thereof is added to an aqueous solution containing HPA and/or a dimer thereof and the resulting mixed solution is subjected to azeotropic distillation, it is possible to minimize a content of HPA and/or a dimer thereof in the resulting distillate and withdraw a concentrated aqueous solution of HPA and/or a dimer thereof as a bottom liquid in an efficient manner. Therefore, the obtained bottom liquid can be reused as the raw material or can be used as an intermediate product of organic compounds such as neopentyl glycol in an industrially advantageous manner.

DESCRIPTION OF EMBODIMENTS

The method for concentrating an aqueous solution containing at least HPA and/or a dimer thereof according to the present invention includes subjecting a mixed solution of an aqueous solution containing at least HPA and/or a dimer thereof and an azeotropic agent to azeotropic distillation in a distillation column to distil off water and the azeotropic agent from the mixed solution, wherein the mixed solution is prepared by adding, as the azeotropic agent, at least one selected from the group consisting of 1-butanol, 2-butanol, 2-methyl-1-propanol, 1-pentanol and 1-hexanol to the aqueous solution.

In the concentrating method of the present invention, the aqueous solution used as a starting solution is not particularly limited as long as it contains HPA and/or a dimer thereof. Also, the content of HPA and/or a dimer thereof in the aqueous solution is not particularly limited. However, the method of the present invention can be suitably used for concentrating an aqueous solution containing HPA and/or a dimer thereof in an amount of from about 1 to about 30% by mass.

In the present invention, the method of synthesizing HPA contained in the aqueous solution as the starting solution is not particularly limited, but, in general, HPA may be produced by an aldol condensation reaction between isobutylaldehyde and formaldehyde or an aqueous formaldehyde solution (formalin) in the presence of a basic catalyst.

Examples of the basic catalyst include inorganic bases such as sodium hydroxide, potassium hydroxide, sodium carbonate and potassium carbonate, and organic bases such as tertiary amines and pyridine. When the basicity of the basic catalyst is excessively high, a Cannizzaro reaction of HPA and/or a dimer thereof with unreacted formaldehyde tends to occur in parallel with the aimed aldol condensation reaction, thereby causing deterioration in yield of HPA and/or a dimer thereof. On the other hand, when the basicity of the basic catalyst is excessively low, the reaction tends to proceed too slowly. From these viewpoints, among the above basic catalysts, tertiary amines are preferably used. Specific examples of the tertiary amines include trimethylamine, triethylamine, tripropylamine, triisopropylamine, tributylamine, triisobutylamine, N-methyl piperidine, N-ethyl piperidine, N-ethyl piperidine, N-methyl morpholine, N-ethyl morpholine, N-methyl pyrrolidine and N-ethyl pyrrolidine. Among these tertiary amines, from the viewpoint of good availability at low costs, preferred are trimethylamine and triethylamine, and more preferred is triethylamine. The suitable amount of the basic catalyst added to the reaction system may vary depending upon the kind thereof. When triethylamine is used as the basic catalyst, the amount of triethylamine added is from 0.001 to 0.5 and preferably from 0.01 to 0.2 on the basis of molar equivalent with respect to isobutylaldehyde.

The method of obtaining the aqueous solution containing HPA and/or a dimer thereof is also not particularly limited. For example, by distillation of a solution produced by the aldol condensation reaction to remove low-boiling point components such as unreacted isobutylaldehyde and formaldehyde therefrom, an aqueous crude HPA solution containing HPA can be obtained. The aqueous crude HPA solution usually contains a monomer and a dimer of HPA.

The thus obtained aqueous crude HPA solution is mixed with a diluent and subjected to crystallization. As the diluent, there may be used water, a filtrate produced upon the solid-liquid separation, a wash liquid obtained by washing crystals produced by crystallization of the reaction product solution with water, or a mixed solution prepared by appropriately combining these liquids. The crystallization may be carried out using seed crystals. The filtrate produced upon the solid-liquid separation after the crystallization usually contains a monomer and a dimer of HPA.

The filtrate contains at least from 1 to 30% by mass of HPA and/or a dimer thereof and from 70 to 99% by mass of water, and preferably from 5 to 15% by mass of HPA and/or a dimer thereof and from 85 to 95% by mass of water. The filtrate may further contain reaction raw materials and reaction by-products in some cases.

In the case where the aqueous solution containing HPA and/or a dimer thereof which is obtained as a filtrate upon the solid-liquid separation is subjected to distillation to remove water therefrom, since HPA forms an azeotropic mixture with water, it is not possible to obtain HPA having a concentration more than that of the azeotropic composition by an ordinary distillation procedure. However, when the aqueous solution is mixed with an azeotropic agent and then the resulting mixture is subjected to distillation, the azeotropic composition of HPA and water is broken, so that water can be recovered from a top of a distillation column. At this time, efficiently concentrated HPA, from which water and impurities such as low-boiling point components are removed, is obtained as a bottom liquid from a bottom of the distillation column.

The concentrating method of the present invention can be especially suitably applied to dehydrative concentration of a filtrate obtained after solid-liquid separation in the HPA purification crystallization, but as described previously, the aqueous solution used as a starting solution is not particularly limited as long as it contains HPA and/or a dimer thereof. Therefore, the method of the present invention may also be applied to dehydrative concentration of an aqueous crude HPA solution and dehydrative concentration of an aqueous solution obtained by dissolving HPA resulting from crystallization purification into water. Accordingly, examples of the aqueous solution containing at least 3-hydroxy-2,2-dimethyl propanal and/or a dimer thereof which may be used in the method of the present invention include the following aqueous solutions (a) to (c):

(a) an aqueous 3-hydroxy-2,2-dimethyl propanal solution obtained by distilling off low-boiling point components including unreacted isobutylaldehyde from a reaction product solution produced by an aldol condensation reaction between an aqueous formaldehyde solution and isobutylaldehyde in the presence of a basic catalyst;

(b) a filtrate recovered by subjecting the aqueous-solution (a) to crystallization, and then subjecting the resultant product to solid-liquid separation; and (c) an aqueous solution obtained by subjecting the aqueous solution (a) to crystallization, then subjecting the resultant product to solid-liquid separation, and then dissolving purified 3-hydroxy-2,2-dimethyl propanal recovered by the solid-liquid separation into water.

Meanwhile, the distillation step of obtaining the aqueous solution (a) is carried out for the purpose of separating HPA from low-boiling point components having a boiling point lower than that of HPA. The low-boiling point components distilled off may include unreacted formaldehyde, methanol if methanol is contained in the aqueous aldehyde solution as the raw material, and a basic catalyst used in the aldol concentration reaction, in addition to the unreacted isobutylaldehyde. The column bottom temperature in the distillation is preferably from 40 to 100° C., and the pressure in the distillation is preferable from 0.1 to 150 kPa.

The above aqueous solutions (a) to (c) may be respectively used alone or in combination of any two or more thereof. In addition, one or more of the aqueous solutions (a) to (c) may be used in the form of a mixture with other liquids.

In the case where a large amount of the catalyst such as a base used upon production of HPA remains in the aqueous solution used as the starting solution, the pH value of the aqueous solution may be appropriately adjusted before an azeotropic agent is mixed therein in order to avoid increase in amount of by-products unexpectedly produced by the reaction between the azeotropic agent and components contained in the aqueous solution.

An acidic compound and a basic compound used for adjusting the pH value of the aqueous solution are not particularly limited. Examples of the acidic compound include inorganic acids and organic acids such as hydrofluoric acid, hydrochloric acid, hydrobromic acid, sulfuric acid, nitric acid, phosphoric acid, boric acid, p-toluenesulfonic acid, methanesulfonic acid, formic acid and acetic acid. Among these acidic compounds, preferred are organic acids such as formic acid by-produced upon the aldol condensation reaction.

Examples of the basic compound include (1) organic amines such as pyridine and triethylamine; (2) hydroxides of alkali metals or alkali earth metals such as sodium hydroxide and calcium hydroxide; (3) carbonates of alkali metals or alkali earth metals such as sodium carbonate, sodium hydrogen carbonate and calcium carbonate; (4) hydrides such as sodium hydride; (5) alkali metal alkyl compounds such as trityl sodium; (6) alkoxides such as sodium methoxide; and (7) amides such as sodium amide. Among these basic compounds, preferred are organic amines used as the basic catalyst upon the aldol condensation reaction, and especially preferred are tertiary amines such as triethylamine. The pH value of the aqueous solution is adjusted to within the range of from 3.5 to 10.5 and preferably from 4.0 to 8.0.

As the azeotropic agent in the present invention, 1-butanol, 2-butanol, 2-methyl-1-propanol, 1-pentanol and 1-hexanol are used alone or in a mixture of two or more thereof. When these compounds are mixed with the aqueous solution containing HPA and/or a dimer thereof, it is possible to break an azeotropic composition of HPA and water. These compounds are capable of forming an azeotropic mixture with water, so that it is possible to efficiently remove water from the aqueous solution while suppressing evaporation of HPA.

Further, the above compounds have a low solubility in water, and therefore the use of these compounds is also advantageous from the industrial viewpoints. More specifically, as a result of the azeotropic distillation, the distillate obtained from a top of the distillation column is readily separated into two phases of an azeotropic agent phase and a water phase. Therefore, the azeotropic agent phase may be fed back into the distillation column and reused therein.

Among the above compounds, preferred are 1-butanol, 2-methyl-1-propanol, 1-pentanol and 1-hexanol. These compounds have a low solubility in water, so that the obtained distillate is easily separated into two phases. Therefore, the use of these compounds is advantageous from the industrial viewpoints. From the further viewpoint of efficiently removing water, among the above compounds, especially preferred are 1-butanol and 2-methyl-1-propanol.

In the case where the azeotropic distillation is carried out using an aliphatic alcohol having 3 or less carbon atoms, a ratio of water in the azeotropic composition of the alcohol and water tends to be reduced, so that a large amount of the azeotropic agent is required to distil off water from the aqueous solution, which results in industrially disadvantageous process. In addition, aliphatic alcohols having 3 or less carbon atoms or some of aliphatic alcohols having 4 or more carbon atoms (for example, 2-methyl-2-propanol) have a high solubility in water. Therefore, since the bottom liquid or distillate is hardly separated into the two phases, it is not possible to recover and reuse the azeotropic agent, which also results in industrially disadvantageous process. Aliphatic alcohols having 7 or more carbon atoms have a less capability of efficiently removing water. Therefore, in the case where the aqueous solution containing HPA and a dimer thereof is subjected to distillation using an aliphatic alcohol having 7 or more carbon atoms, a large amount of HPA tends to be included in the distillate, which also results in industrially disadvantageous process.

The distillation method used for subjecting the mixed solution of the aqueous solution containing HPA and/or a dimer thereof and the azeotropic agent to azeotropic distillation in a distillation column to distil off water and the azeotropic agent from the mixed solution may be either a batch method or a continuous method. The pressure used in the distillation purification is not particularly limited, and the distillation purification may be carried out either under normal pressures or under reduced pressure. The distillation column used in the present invention is also not particularly limited, and a multistage distillation column is preferably used. When the distillation column is a tray column, any type of a tray such as a bubble cap tray, a sieve tray, a Uniflux tray, a valve tray, a Natta valve tray, a ballast tray, a venturi tray, a Kitter tray, a turbo grid tray and a ripple tray may be adopted. The distillation column may also be a packed column. As the packing used in the packed column, any type of packing, e.g., ring type packing such as Raschig ring, Lessing ring, split ring and Pall ring, saddle type packing such as bar saddle and interlock saddle, Goodroy packing, Stedman packing, Dixon ring, Magmahon packing, helix packing, Tellerrette packing, cross spiral packing, etc may be adopted. The stage to which the raw materials are fed is not particularly limited.

The content of the azeotropic agent in the mixed solution of the aqueous solution containing HPA and/or a dimer thereof and the azeotropic agent may be appropriately determined in view of both of a capability of efficiently removing water and a capability of recovering the azeotropic agent from a bottom liquid in an industrially efficient manner. In the case where the content of the azeotropic agent in the mixed solution is excessively small, removal of water by the azeotropic distillation tends to become insufficient. On the other hand, in the case where the content of the azeotropic agent in the mixed solution is excessively large, it is required to recover a large amount of the azeotropic agent from a bottom liquid obtained after the concentration, which tends to result in industrially disadvantageous procedure. The suitable content of the azeotropic agent in the mixed solution may vary depending upon the kind of azeotropic agent used and may be appropriately determined in view of the aforementioned points, and in general is preferably not less than 5% by mass and not more than 50% by mass, and more preferably not less than 10% by mass and not more than 45% by mass. For example, when 2-methyl-1-propanol is used as the azeotropic agent, the content of the azeotropic agent in the above mixture is preferably more than 6.18% by mass and not more than 50% by mass.

The column bottom temperature for subjecting the mixed solution of the aqueous solution containing HPA and/or a dimer thereof and the azeotropic agent to azeotropic distillation in a distillation column to distil off water and the azeotropic agent from the mixed solution is suitably controlled so that the mixed solution may not become solidified. The column bottom temperature is preferably in the range of from 82 to 120° C. and more preferably from 85 to 110° C.

When the column bottom temperature is lower than 82° C., the mixed solution of the aqueous solution and the azeotropic agent present at the bottom of the distillation column may be solidified, which may result in obstacle to the concentration Also, the column bottom temperature is preferably 120° C. or lower in order to suppress production of an esterification product compound between HPA molecules represented by the formula (2) (a hydroxypivalic acid neopentyl glycol monoester) as a by-product.

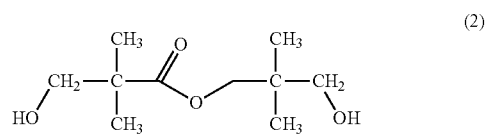

The azeotrope: agent contained in the distillate obtained from a top of the distillation column upon the azeotropic distillation may be separated from the distillate and reused. From the industrial viewpoints, it is advantageous to repeatedly use the azeotropic agent by the reuse.

More specifically, the concentrating method of the present invention preferably further includes obtaining a distillate from a top of the distillation column; and feeding, after the distillate is separated into two phases of an azeotropic agent phase and a water phase, a whole or part of the azeotropic agent phase back into the distillation column. Meanwhile, the distillate may be hardly separated into the two phases owing to a certain kind of azeotropic agent used. In such a case, the distillate may be cooled to achieve separation thereof into the two phases.

EXAMPLES

The present invention will be described in more detail below by referring to the following examples. It should be noted, however, that the following examples are only illustrative and not intended to limit the invention thereto. Composition analysis was performed by gas chromatography. HPA and a dimer thereof were not distinguished from each other in the gas chromatography and therefore totally evaluated as to a mixture thereof.

[Conditions of Gas Chromatography]

Sample to be measured: A sample was prepared in the form of a ca. 1% by mass acetone solution.

Apparatus: "GC-6890N" (available from Agilent Technologies Corp.)

Column used: "DB-1" (available from Agilent Technologies Corp.)

Analyzing Conditions: Injection temperature: 200° C.

Detector temperature: 250° C.

Column Temperature: Held at 60° C. for 7 min→Raised to 250° C. at a rate of 6° C./min→Held at 250° C. for 20 min Detector: Flame ionization detector (FID)

[Concentration of HPA in Distillate]

The concentration of HPA in the distillate was calculated by subtracting an amount of the azeotropic agent contained in the distillate from an amount of the distillate.

[Concentration of HPA in Bottom Liquid]

The concentration of HPA in the bottom liquid obtained after the azeotropic distillation was calculated by subtracting an amount of the azeotropic agent contained in the bottom liquid from an amount of the bottom liquid.

Reference Example 1

Preparation of Aqueous HPA Solution

While 200 parts by mass of isobutylaldehyde (1st grade reagent; available from Wako Pure Chemical Industries, Ltd.) and 225 parts by mass of 40% by mass formalin (available from Mitsubishi Gas Chemical Co., Inc.) were stirred, 9.9 parts by mass of triethylamine (guaranteed reagent; available from Wako Pure Chemical Industries, Ltd.) was added thereto as a catalyst to conduct an aldol condensation reaction. The resulting reaction solution was subjected to distillation at a temperature of from 70 to 80° C. under a pressure of 40 kPa to distil off low-boiling point components such as unreacted isobutylaldehyde and triethylamine, thereby obtaining 425 part by mass of an aqueous crude HPA solution. As a result of analyzing a composition of the resulting aqueous crude HPA solution, it was confirmed that the aqueous crude HPA solution had the following composition: HPA: 62.1% by mass; neopentyl glycol: 1.53% by mass; formaldehyde: 1.60% by mass; triethylamine: 1.30% by mass; formic acid: 0.41% by mass; hydroxypivalic acid neopentyl glycol monoester: 0.95% by mass; water: 28.5% by mass; and other components: 3.61% by mass.

Reference Example 2

Crystallization of Aqueous Crude HPA Solution

A crystallization vessel was charged with 260 parts by mass of the aqueous crude HPA solution obtained in Reference Example 1 and 590 parts by mass of water to prepare a solution containing HPA and/or a dimer thereof at a concentration of 19.0% by mass. While being stirred, the resulting solution was cooled to 40° C. and then subjected to crystallization at a temperature of from 39 to 40° C. The crystallization was terminated after the elapse of 90 min. Thereafter, a whole amount of the resulting slurry was subjected to solid-liquid separation using a centrifugal separator. At this time, the obtained cake was washed with 100 parts by mass of water. As a result, 857.5 parts by mass of a filtrate were recovered, and 91.9 parts by mass of the filter cake were obtained. The thus obtained cake was dried at 30° C. under a nitrogen gas flow, thereby obtaining 71.3 parts by mass of crystals of HPA and/or a dimer thereof. The recovery rate of HPA and/or a dimer thereof was 44.1%. As a result of analyzing the crystals of HPA and/or a dimer thereof by gas chromatography, it was confirmed that the crystals of HPA and/or a dimer thereof had a purity of 99.0%. In addition, as a result of analyzing a composition of the filtrate obtained by the solid-liquid separation, it was confirmed that the filtrate had the following composition: HPA: 10.9% by mass; neopentyl glycol: 0.25% by mass; formaldehyde: 0.36% by mass; triethylamine: 0.30% by mass; formic acid: 0.12% by mass; hydroxypivalic acid neopentyl glycol monoester: 0.49% by mass; water: 86.8% by mass; and other components: 0.78% by mass. Further, the pH value of the filtrate was 4.8.

Example 1

In the Case of Using 2-methyl-1-propanol as an Azeotropic Agent

As a distillation apparatus, a 500 mL flask connected with a condenser and a Dean-Stark trap was used. The 500 mL flask was charged with a mixed solution prepared by mixing 240 parts by mass of the filtrate recovered in Reference Example 2 and 160 parts by mass of guaranteed 2-methyl-1-propanol available from Wako Pure Chemical Industries, Ltd., as an azeotropic agent. Next, the column bottom temperature of the distillation column (flask) was adjusted to within the range of from 90 to 106° C., and the mixed solution was subjected to azeotropic distillation under normal pressures while being stirred. A whole amount of an azeotropic agent phase in the resulting distillate was refluxed, and only a water phase therein was sampled. As a result, 34.0% by mass of the filtrate charged were distilled off. The concentration of HPA in the water phase in the distillate thus obtained and the concentration of HPA in a bottom liquid obtained after the distillation are shown in Table 1.

Examples 2 to 4

In the Case of Using 1-butanol, 1-pentanol or 1-hexanol as an Azeotropic Agent

The same procedure as in Example 1 was repeated except for using guaranteed 1-butanol, 1-pentanol or 1-hexanol available from Wako Pure Chemical Industries, Ltd., in place of 2-methyl-1-propanol. The results are shown in Table 1.

Comparative Examples 1 to 3

In the Case of Using 1-heptanol, 2-ethyl hexanol or o-xylene as an Azeotropic Agent The same procedure as in Example 1 was repeated except for using guaranteed 1-heptanol, 2-ethyl hexanol or o-xylene available from Wako Pure Chemical Industries, Ltd., in place of 2-methyl-1-propanol. The results are shown in Table 1.

TABLE 1

| | Azeotropic agent | Concentration of HPA in water phase of distillate (except for azeotropic agent) (mass %) | Concentration of HPA in bottom liquid (except for azeotropic agent) (mass %) | Condition of distillate |
|---|---|---|---|---|
| Example 1 | 2-Methyl-1-propanol | 0.07 | 16.5 | Separated into two phases |
| Example 2 | 1-Butanol | 0.12 | 16.5 | Separated into two phases |
| Example 3 | 1-Pentanol | 0.30 | 16.4 | Separated into two phases |
| Example 4 | 1-Hexanol | 0.76 | 16.1 | Separated into two phases |
| Comparative Example 1 | 1-Heptanol | 1.58 | 15.7 | Separated into two phases |
| Comparative Example 2 | 2-Ethyl hexanol | 1.99 | 15.5 | Separated into two phases |
| Comparative Example 3 | o-Xylene | 2.52 | 15.2 | Separated into two phases |

As shown in Table 1, it was confirmed that when 2-methyl-1-propanol, 1-butanol, 1-pentanol or 1-hexanol was used as an azeotropic agent, it was possible to reduce a concentration of HPA in the water phase of the distillate and as a result, considerably reduce a disadvantageous discharge of the useful HPA as a distillate.

Comparative Example 4

In the Case of Using 2-methyl-2-propanol as an Azeotropic Agent

As a distillation apparatus, a 500 mL flask connected with a condenser was used. The 500 mL flask was charged with a mixed solution prepared by mixing 240 parts by mass of the filtrate recovered in Reference Example 2 and 160 parts by mass of guaranteed 2-methyl-2-propanol available from Wako Pure Chemical Industries, Ltd. Next, the mixed solution was subjected to azeotropic distillation under normal pressures while being stirred. The column bottom temperature of the distillation column was 90° C. After from 10 to 12% by mass of the charged filtrate was distilled off, the column bottom temperature began to rise and therefore the distillation procedure was terminated. A whole amount of the distillate was recovered because it was not separated into two phases. At this time, it was confirmed that the concentration of HPA in the distillate was 0.50% by mass.

Example 5

Multistage Distillation Using 2 methyl-1-propanol as an Azeotropic agent

As a distillation apparatus, used was a 3 L flask connected with a packed column being filled with Raschig rings and having a theoretical plate number of 8 which was further connected at a top thereof with a Dean-Stark trap and a condenser. The flask was charged with a mixed solution prepared by mixing 694 parts by mass of the filtrate recovered in Reference Example 2 and 484 parts by mass of guaranteed 2-methyl-1-propanol available from Wako Pure Chemical Industries, Ltd. Next, the mixed solution was subjected to azeotropic distillation under normal pressures while being stirred. The column bottom temperature of the distillation column was 91° C. At this time, the distillate was separated into two phases. A whole amount of an azeotropic agent phase containing a large amount of 2-methyl-1-propanol in the resulting distillate was refluxed, and only a water phase therein was sampled. The water phase of the distillate, when 34.3% by mass on the basis of the charged filtrate was recovered, had the following composition: HPA: 0.01% by mass; water: 99.9% by mass; and other components: 0.09% by mass. The concentration of HPA in a bottom liquid obtained after the distillation was 16.6% by mass.

Comparative Example 5

Multistage Distillation Using No Azeotropic Agent

As a distillation apparatus, used was a 3 L flask connected with the same packed column as used in Example 5 which was further connected at a top thereof with a refluxing device and a condenser. The 3 L flask was charged with 1743 parts by mass of the filtrate recovered in Reference Example 2 only. Next, the filtrate was subjected to distillation under normal pressures at a reflux ratio of 1 while being stirred. The column bottom temperature of the distillation column was 101° C. The distillate, when 33.9% by mass of the charged filtrate was distilled off, had the following composition: HPA: 5.10% by mass; water: 93.9% by mass; and other components: 1.00% by mass. The concentration of HPA in a bottom liquid obtained after the distillation was 13.9% by mass.

Example 6

Confirmation of Upper Limit of Content of Azeotropic Agent in Bottom Liquid of Distillation Apparatus As a distillation apparatus, used was a 3 L flask connected with the same packed column as used in Example 5 which was further connected at a top thereof with a refluxing device and a condenser. The flask was charged with a mixed solution prepared by mixing 857 parts by mass of the filtrate recovered in Reference Example 2 and 359 parts by mass of -2-methyl-1-propanol (guaranteed reagent: available from Wako Pure Chemical Industries, Ltd.). Next the mixed solution was subjected to azeotropic distillation under normal pressures at a reflux ratio of 1 while being stirred. The column bottom temperature of the distillation column was 91° C. At this time, a whole amount of the distillate was recovered although it was separated into two phases. After 452 parts by mass of the distillate was distilled off, the column bottom temperature began to rise and the concentration of HPA in the distillate also began to rise. At this time, the concentration of 2-methyl-1-propanol in the bottom liquid was 6.18% by mass. Therefore, it was conformed that when 2-methyl-1-propanol was used as an azeotropic agent, it was preferred to maintain a concentration of the azeotropic agent in the mixed solution of the aqueous solution containing HPA and/or a dimer thereof and the azeotropic agent at a level of more than 6.18% by mass in order to minimize an amount of HPA included in the distillate.

INDUSTRIAL APPLICABILITY

HPA is an intermediate product for synthesis of organic compounds such as neopentyl glycol, a 2,2-dimethyl-1,3-propanediol hydroxypivalic acid monoester, hydroxypivalic acid, Spiro glycol and dioxane glycol. When an aqueous solution containing HPA and/or a dimer thereof is subjected to dehydrative distillation in the presence of an azeotropic agent in an efficient manner according to the method of the present invention, the obtained bottom liquid can be advantageously reused as a raw material for an intermediate product of the above organic compounds. Therefore, the present invention has a large industrial significance.

The invention claimed is:

1. A method for concentrating an aqueous solution containing at least 3-hydroxy-2,2-dimethyl propanal and/or a dimer thereof, comprising
subjecting a mixed solution of an aqueous solution containing at least 3-hydroxy-2,2-dimethyl propanal and/or a dimer thereof and an azeotropic agent to azeotropic distillation in a distillation column to distil off water and the azeotropic agent from the mixed solution, wherein the mixed solution is prepared by adding, as the azeotropic agent, at least one selected from the group consisting of 1-butanol, 2-butanol, 2-methyl-1-propanol, 1-pentanol and 1-hexanol to the aqueous solution.

2. The method according to claim 1, wherein the azeotropic agent is at least one selected from the group consisting of 1-butanol and 2-methyl-1-propanol.

3. The method according to claim 1, wherein the 3-hydroxy-2,2-dimethyl propanal and/or the dimer thereof are produced by an aldol condensation reaction between formaldehyde and isobutylaldehyde.

4. The method according to claim 1, wherein the aqueous solution containing at least 3-hydroxy-2,2-dimethyl propanal and/or a dimer thereof is an aqueous solution containing at least one selected from the group consisting of the following (a) to (c):
   (a) an aqueous 3-hydroxy-2,2-dimethyl propanal solution obtained by distilling off low-boiling point components including unreacted isobutylaldehyde from a reaction product solution produced by an aldol condensation reaction between an aqueous formaldehyde solution and isobutylaldehyde in the presence of a basic catalyst;
   (b) a filtrate recovered by subjecting the aqueous solution (a) to crystallization, and then subjecting the resultant product to solid-liquid separation; and
   (c) an aqueous solution obtained by subjecting the aqueous solution (a) to crystallization, then subjecting the resultant product to solid-liquid separation, and then dissolving purified 3-hydroxy-2,2-dimethyl propanal recovered by the solid-liquid separation into water.

5. The method according to claim 1, wherein the azeotropic distillation is carried out at a column bottom temperature of from 82 to 120° C.

6. The method according to claim 1, further comprising
obtaining a distillate from a top of the distillation column; and
feeding, after the distillate is separated into two phases of an azeotropic agent phase and a water phase, a whole or part of the azeotropic agent phase back into the distillation column.

7. The method according to claim 1, wherein the distillation column is a multistage distillation column.

8. The method according to claim 1, further comprising
adjusting a pH value of the aqueous solution containing at least 3-hydroxy-2,2-dimethyl propanal and/or a dimer thereof to within a range of from 3.5 to 10.5.

9. The method according to claim 3, wherein the azeotropic agent is at least one selected from the group consisting of 1-butanol and 2-methyl-1-propanol.

10. The method according to claim 4, wherein the azeotropic agent is at least one selected from the group consisting of 1-butanol and 2-methyl-1-propanol.

11. The method according to claim 5, wherein the azeotropic agent is at least one selected from the group consisting of 1-butanol and 2-methyl-1-propanol.

12. The method according to claim 6, wherein the azeotropic agent is at least one selected from the group consisting of 1-butanol and 2-methyl-1-propanol.

13. The method according to claim 7, wherein the azeotropic agent is at least one selected from the group consisting of 1-butanol and 2-methyl-1-propanol.

14. The method according to claim 8, wherein the azeotropic agent is at least one selected from the group consisting of 1-butanol and 2-methyl-1-propanol.

15. The method according to claim 1, wherein the azeotropic agent is at least one selected from the group consisting of 1-butanol, 2-butanol, 2-methyl-1-propanol, and 1-pentanol.

16. The method according to claim 3, wherein the azeotropic agent is at least one selected from the group consisting of 1-butanol, 2-butanol, 2-methyl-1-propanol, and 1-pentanol.

17. The method according to claim 4, wherein the azeotropic agent is at least one selected from the group consisting of 1-butanol, 2-butanol, 2-methyl-1-propanol, and 1-pentanol.

18. The method according to claim 5, wherein the azeotropic agent is at least one selected from the group consisting of 1-butanol, 2-butanol, 2-methyl-1-propanol, and 1-pentanol.

19. The method according to claim 6, wherein the azeotropic agent is at least one selected from the group consisting of 1-butanol, 2-butanol, 2-methyl-1-propanol, and 1-pentanol.

20. The method according to claim 7, wherein the azeotropic agent is at least one selected from the group consisting of 1-butanol, 2-butanol, 2-methyl-1-propanol, and 1-pentanol.

* * * * *